United States Patent

Soldati

[11] 4,041,028
[45] Aug. 9, 1977

[54] CHLORINATION OF 2,3-DIMETHYL-1,2,4-BENZOTHIA-DIAZINE 1,1-DIOXIDE

[75] Inventor: Gianluigi Soldati, Mercerville, N.J.

[73] Assignee: Carter-Wallace, Inc., New York, N.Y.

[21] Appl. No.: 571,425

[22] Filed: Apr. 24, 1975

[51] Int. Cl.² .......................................... C07D 279/08
[52] U.S. Cl. ...................................... 544/12; 260/694
[58] Field of Search ............................ 260/243 D, 694

[56] References Cited

U.S. PATENT DOCUMENTS

| | | | |
|---|---|---|---|
| 3,123,608 | 3/1964 | Mathes et al. | 260/694 |
| 3,244,722 | 4/1966 | Johnston et al. | 260/290 HL |
| 3,297,693 | 1/1967 | de Stevens et al. | 260/243 D |
| 3,351,595 | 11/1967 | de Stevens et al. | 260/243 D |
| 3,644,348 | 2/1972 | Irikura et al. | 260/243 D |
| 3,666,644 | 5/1972 | Kollonitsch et al. | 260/694 |

FOREIGN PATENT DOCUMENTS 912,126  12/1962  United Kingdom ............ 260/243 D

*Primary Examiner*—Donald G. Daus
*Assistant Examiner*—D. B. Springer
*Attorney, Agent, or Firm*—Kevin B. Clarke

[57] ABSTRACT

Novel 2,3-disubstituted-1,2,4-benzothiadiazine 1,1-dioxides of the formula:

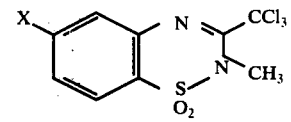

wherein X is hydrogen or chlorine. The novel compositions have been obtained by an unexpected side chain chlorination and have been found to be useful in medicinal chemistry as antihypertensives.

1 Claim, No Drawings

CHLORINATION OF 2,3-DIMETHYL-1,2,4-BENZOTHIA-DIAZINE 1,1-DIOXIDE 1,2,4-benzothiadiazine 1,1-dioxides may be prepared according to J. H. Friedman and E. C. Wagner, J. Org. Chem., 16, 815 (1951) by the condensation of a substituted o-aminobenzenesulfonamide with the appropriate orthoester.

Similarly various 3-substituted 2H-1,2,4-benzothiadiazine 1,1-dioxides are obtained by utilizing the known method of fusing the appropriately substituted o-acylaminobenzenesulfonamides as described by A. Ekbom, Bihang Till Svenska Vet. Akad. Handl., 27 (II), 3 (1902) and F. C. Novello, S. C. Bell, E. L. A. Abrams, C. Ziegler, and J. M. Sprague, J. Org. Chem. 25, 970 (1960).

Also acylaminobenzenesulfonamides are converted to 1,2,4-benzothiadiazine 1,1-dioxides by the action of alkali as reported by L. Raffa, II Farmaco, Ed. Sci, 12, 279 (1957).

We have found that direct halogenation can be applied to 2,3-dialkyl-1,2,4-benzothiadiazine 1,1-dioxides.

The reported chlorination (L. Raffa et. al., II Farmaco, Ed. Sci., 17, 234 (1962) of 3-alkyl-2H-1,2,4-benzothiadiazine 1,1-dioxide (I) yields the corresponding 7-chloro derivative (II). Similarly 3-oxo-3,4-dihydro-1,2,4-benzothiadiazine 1,1-dioxide (III) yields a 7-chloro derivative (IIIa) or a 5,7-dichloro derivative (IIIb) depending on reaction conditions.

EXAMPLE I

2-METHYL-3-TRICHLOROMETHYL-1,2,4-BENZOTHIADIAZINE 1,1-DIOXIDE.

In a three neck round-bottom flask, equipped with stirrer, thermometer and gas inlet, 4g. of 2,3-dimethyl-1,2,4-benzothiadiazine 1,1-dioxide are dissolved in 14 ml of dimethylformamide. Chlorine is slowly added to the stirred solution, the temperature being allowed to rise to 45°. As soon as 4 g. of chlorine are absorbed, the gas inlet is removed and the dark yellow solution allowed to stand for thirty minutes. The solution is then poured into crushed ice. A gummy product separates. The water is decanted and a small amount of 50% aqueous methanol is added. The gum solidifies on treaturation. The product is collected to give 4.2 g of white crystals melting at 135°–137° after one recrystallization from methanol. Analysis: calculated for $C_9H_7Cl_3N_2O_2S$: C%, 34.47; H, 2.25; N, 8.93. Found C, 34.86; H, 2.21; N, 8.95.

N.M.R. analysis of this material in acetone-$d_6$ gives a proton count of seven, showing four protons for the benzene ring at 8 ppm and a three proton singlet at 3.75 ppm for the methyl in the 2 position.

EXAMPLE II

6-CHLORO-2-METHYL-3-TRICHLOROMETHYL-1,2,4-BENZOTHIADIAZINE 1,1-DIOXIDE.

16 g. of 6-chloro-2,3-dimethyl-1,2,4-benzothiadiazine 1,1-dioxide, dissolved in 50 ml of dimethylformamide are treated with 16 g. of chlorine at 55°–80° C. On Re-

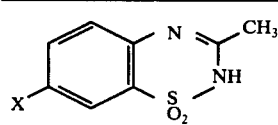
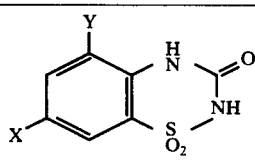
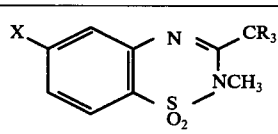

| X | | X | Y | | R | X | |
|---|---|---|---|---|---|---|---|
| H | I | H | H | III | H | H | IV |
| Cl | II | Cl | H | IIIa | Cl | H | IVa |
| | | Cl | Cl | IIIb | H | Cl | V |
| | | | | | Cl | Cl | Va |

We have found that when 2,3-dimethyl-1,2,4-benzothiadiazine 1,1-dioxides (IV and V) are halogenated as reported with chlorine in dimethylformamide do not undergo ring chlorination as expected but in fact yielded the novel 3-trichloromethyl derivatives (IVa and Va).

The novel compositions herein described may then be represented by the general formula:

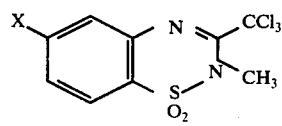

wherein X may be hydrogen or chlorine. The yield of these new 1,2,4-benzothiadiazine 1,1-dioxide is considerably increased by higher reaction temperatures or by the presence of ultraviolet light. Halogenation is best carried out at 40°–60°.

crystallization of the crude material from benzene-hexane a crystalline product melting at 145°–6° C was obtained.

N.M.R. analysis in acetone-$d_6$ showed a singlet at 3.75 ppm for the methyl group and three protons for the ring at 7.75–8.2 ppm.

Analyzed for $C_9H_6Cl_4N_2O_2S$: C, 31.06; H, 1.74; N, 8.05. Found: C, 31,23; H, 1.92; N, 7.81.

The novel compounds of the present invention exhibit antihypertensive properties in warm-blooded animals and may be used in the manner ordinarily employed by those taking advantage of the aforementioned activity. Thus the compounds can be admixed with commonly used and medically accepted solvents, suspension media, surfactants, carriers, extenders and diluents; they also can be combined with other compounds or commercial preparations which possess like properties or enhance the aforementioned activity.

It is to be understood that those variations of the invention which are within the competence of those skilled in the art and which basically rely on the teaching described herein are considered to be within the scope of the description and appended claims.

What is claimed is:

1. A process for preparing a compound selected from the group consisting of 2-methyl-3-trichloromethyl-1,2,4-benzothiadiazine-1,1-dioxide and 6-chloro-2-methyl-3-trichloromethyl-1,2,4-benzothiadiazine-1,1-dioxide which comprises dissolving a compound of the formula:

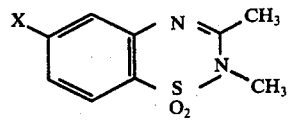

Wherein X is hydrogen or chlorine, in dimethylformamide and chlorinating with chlorine at 45°–80° C, and recovering the desired product.